(12) United States Patent
Govari et al.

(10) Patent No.: US 11,109,774 B2
(45) Date of Patent: *Sep. 7, 2021

(54) FLAT LOCATION PAD USING NONCONCENTRIC COILS

(71) Applicant: Biosense Webster (Israel) Ltd., Yokneam (IL)

(72) Inventors: Assaf Govari, Haifa (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 1032 days.

This patent is subject to a terminal disclaimer.

(21) Appl. No.: 15/059,628

(22) Filed: Mar. 3, 2016

(65) Prior Publication Data

US 2017/0007156 A1 Jan. 12, 2017

Related U.S. Application Data

(63) Continuation-in-part of application No. 14/791,667, filed on Jul. 6, 2015.

(51) Int. Cl.
*A61B 5/06* (2006.01)
*A61B 34/20* (2016.01)
(Continued)

(52) U.S. Cl.
CPC .............. *A61B 5/062* (2013.01); *A61B 34/20* (2016.02); *H01F 27/2823* (2013.01); *A61B 6/487* (2013.01); *A61B 2034/2051* (2016.02); *A61B 2034/2072* (2016.02); *A61B 2034/731* (2016.02); *A61B 2090/376* (2016.02); *A61B 2562/17* (2017.08)

(58) Field of Classification Search
CPC ......... A61B 5/062; A61B 5/6801; A61B 5/68; A61B 5/061–068; A61B 34/20; A61B 6/487; A61B 2034/2046; A61B 2034/2072; A61B 2034/2051; H01F 27/2823
See application file for complete search history.

(56) References Cited

U.S. PATENT DOCUMENTS 5,307,072 A * 4/1994 Jones, Jr. .................. F41G 3/08
324/244
5,391,199 A 2/1995 Ben-Haim
(Continued)

FOREIGN PATENT DOCUMENTS

CN 101069641 A 11/2007
EP 1266610 A2 12/2002
(Continued)

OTHER PUBLICATIONS

European Search Report, Application No. 16178006.9-1657, dated Nov. 28, 2016.
(Continued)

*Primary Examiner* — Sean D Mattson
(74) *Attorney, Agent, or Firm* — Notaro, Michalos & Zaccaria P.C.

(57) ABSTRACT

A field generator includes multiple planar coils that are arranged in a single plane. At least two of the coils are non-concentric and are wound around respective axes that are not parallel with one another, so as to generate respective magnetic fields that are not parallel with one another.

7 Claims, 3 Drawing Sheets

(51) Int. Cl.
*H01F 27/28* (2006.01)
*A61B 6/00* (2006.01)
*A61B 90/00* (2016.01)
*A61B 34/00* (2016.01)

(56) References Cited

U.S. PATENT DOCUMENTS

| | | | |
|---|---|---|---|
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,701,179 | B1* | 3/2004 | Martinelli ............... A61B 90/36 600/424 |
| 8,180,430 | B2 | 5/2012 | Govari et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2004/0199072 | A1 | 10/2004 | Sprouse |
| 2005/0085715 | A1* | 4/2005 | Dukesherer ............... A61B 5/06 600/424 |
| 2006/0004286 | A1 | 1/2006 | Chang |
| 2007/0078334 | A1* | 4/2007 | Scully ..................... A61B 5/06 600/424 |
| 2007/0265526 | A1 | 11/2007 | Govari et al. |
| 2008/0033282 | A1* | 2/2008 | Bar-Tal .................. A61B 5/062 600/424 |
| 2008/0174303 | A1 | 7/2008 | Anderson |
| 2009/0043188 | A1* | 2/2009 | Rauscher ............... A61N 1/326 600/409 |
| 2014/0275998 | A1 | 9/2014 | Eichler |
| 2017/0007156 | A1 | 1/2017 | Govari |

FOREIGN PATENT DOCUMENTS

| | | |
|---|---|---|
| EP | 1854405 A1 | 11/2007 |
| EP | 3114996 B1 | 10/2019 |
| JP | 2004275776 A | 10/2004 |
| JP | 2008062040 A | 3/2008 |
| WO | WO 96/05768 | 2/1996 |
| WO | 9729683 A1 | 8/1997 |

OTHER PUBLICATIONS

European Search Report, Application No. 16178004.4-1657, dated Nov. 28, 2016.

U.S. Appl. No. 14/791,667, filed Jul. 6, 2015.

* cited by examiner

FLAT LOCATION PAD USING NONCONCENTRIC COILS

CROSS-REFERENCE TO RELATED APPLICATIONS

This application is a continuation-in-part of U.S. patent application Ser. No. 14/791,667, filed Jul. 6, 2015, whose disclosure is incorporated herein by reference.

FIELD OF THE INVENTION

The present invention relates generally to position tracking systems, and specifically to location pads used in magnetic position tracking.

BACKGROUND OF THE INVENTION

Magnetic position tracking systems are used in a wide range of medical applications, such as in minimally invasive procedures. Examples of prior art techniques are provided below.

U.S. Patent application publication 2007/0265526, to Govari, et al., whose disclosure is incorporated herein by reference, describes a magnetic position tracking system for performing a medical procedure on a patient who is positioned on an upper surface of a table includes a location pad, which is positioned on the upper surface of the table beneath the patient. The location pad includes one or more field-generators, which are operative to generate respective magnetic fields and are arranged so that a thickness dimension of the location pad is no greater than 3 centimeters. A position sensor is fixed to an invasive medical device for insertion into a body of the patient, and is arranged to sense the magnetic fields so as to measure a position of the medical device in the body.

U.S. Pat. No. 8,180,430, to Govari, et al., whose disclosure is incorporated herein by reference, describes a method for position tracking, including using first and second field-generators located at respective different first and second locations to generate respective first and second magnetic fields in a vicinity of first and second objects.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention that is described herein provides a field generator including multiple planar coils that are arranged in a single plane. At least two of the coils are non-concentric and are wound around respective axes that are not parallel with one another, so as to generate respective magnetic fields that are not parallel with one another.

In some embodiments, at least two of the magnetic fields are oriented in mutually-orthogonal directions. In other embodiments, the non-concentric coils are arranged side-by-side in the single plane. In yet other embodiments, the at least two coils include respective cores oriented at the respective axes, and respective wires wound around the cores. In an embodiment, the cores include carbon. In another embodiment, each of the at least two coils has a thickness between 6 mm and 10 mm.

There is additionally provided, in accordance with an embodiment of the present invention, a method for producing a field generator including providing multiple planar coils. The planar coils are arranged in a single plane, such that at least two of the coils are non-concentric and the coils are wound around respective axes that are not parallel with one another.

There is additionally provided, in accordance with an embodiment of the present invention, a method for generating magnetic fields including providing a field generator, including multiple planar coils that are arranged in a single plane. At least two of the coils are non-concentric and are wound around respective axes that are not parallel with one another. Electrical currents are driven into the multiple planar coils so as to generate respective magnetic fields that are not parallel with one another.

The present disclosure will be more fully understood from the following detailed description of the embodiments thereof, taken together with the drawings, in which:

DETAILED DESCRIPTION OF EMBODIMENTS

Overview

Intra-body probes, such as catheters, are used in various therapeutic and diagnostic medical procedures. The probe is inserted into the living body of a patient and navigated to the target region in a body cavity to perform the medical procedure. In some magnetic-field-based position tracking systems, an external magnetic field is applied to the patient's body. A position sensor installed near the distal end of the catheter responds to the field by producing an electrical signal. The tracking system uses the signal to locate the position and orientation of the catheter relative to the patient's body. The magnetic field is typically produced by multiple field-generators, e.g., field-generating coils, fixed on a surface so as to form a location pad.

In some scenarios, it is desirable to operate a fluoroscopic system simultaneously with the magnetic position tracking system, in order to acquire an image of a region-of-interest (ROI) of the organ in question. In an intra-cardiac procedure, for example, the ROI of both systems comprises the left-hand-side of the patient's chest. In such scenarios, parts of the location pad of the magnetic position tracking system may fall within the Field-Of-View (FOV) of the fluoroscopic system, and may block or obscure portions of the fluoroscopic image.

Embodiments of the present invention that are described herein provide open-frame and low-profile (e.g., thin) location pad configurations. The disclosed location pads comprise multiple magnetic field-generators (e.g., planar coils) that are fixed on a frame (e.g., a triangle or a rectangle frame) at respective positions surrounding the ROI. The frame is open on at least one side of the ROI, typically the side facing the fluoroscopic system. As a result, the location pad causes little or no obstruction to the fluoroscopic imaging, at least in fluoroscopic projections that are commonly used in cardiac procedures.

The disclosed location pads have a low profile, e.g., a thickness on the order of 1.2 cm. Such a location pad can be easily placed between a moving table (on which the patient is positioned) and the patient's body, as opposed to conventional location pads that are thicker and have to be placed below the table.

In an embodiment, each of the field-generators comprises three concentric planar coils that are configured in non-parallel directions (e.g., orthogonally) relative to one another so as to generate magnetic field components in three respective non-parallel (e.g., orthogonal) directions. In an alternative embodiment, at least two of the planar coils (e.g., all three coils) are arranged in a non-concentric configuration, e.g., side-by-side in a single plane, so as to reduce the thickness of the field-generator.

SYSTEM DESCRIPTION

Figure 1:
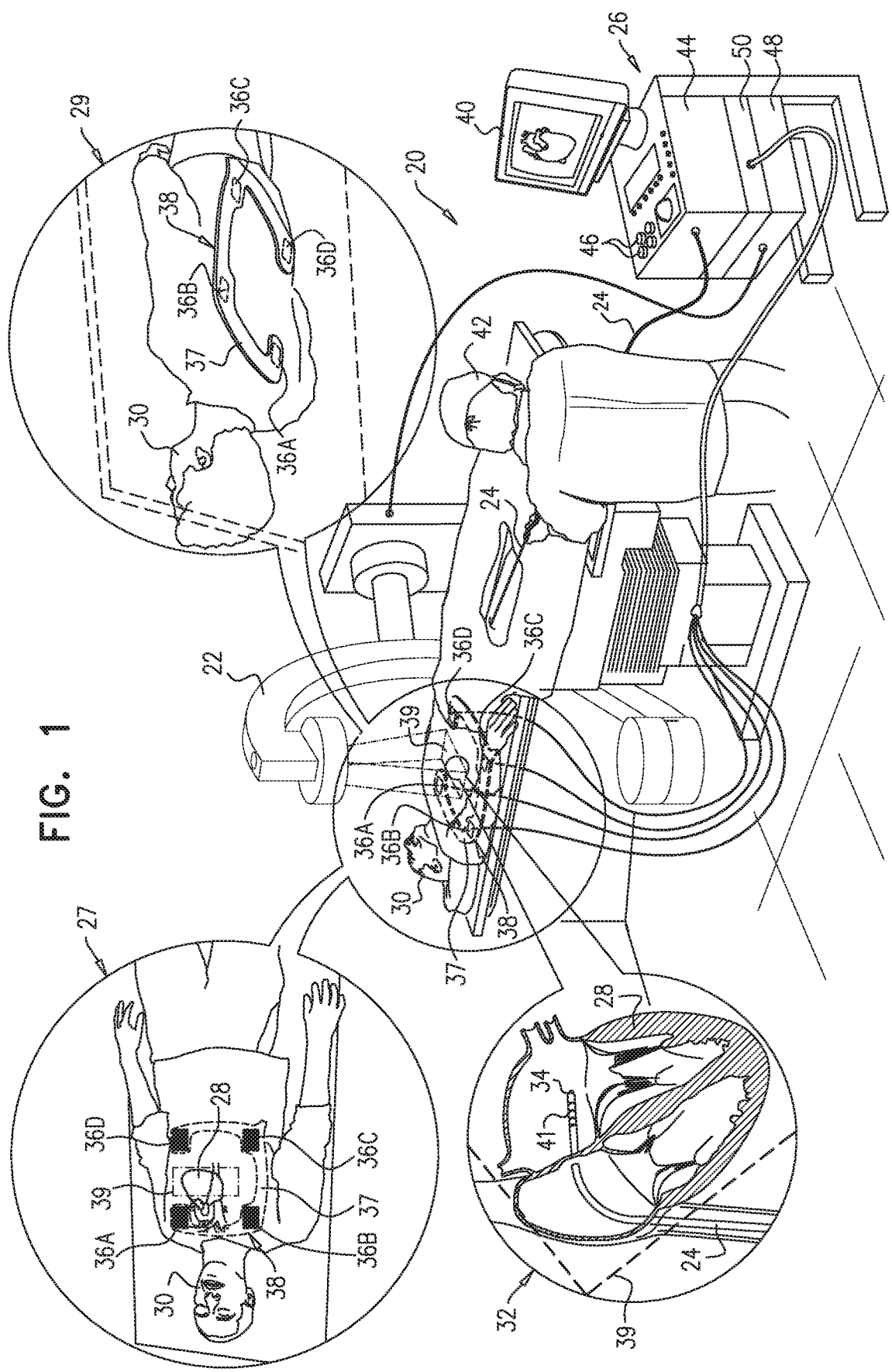
FIG. 1 is a schematic pictorial illustration of a fluoroscopic imaging system and a magnetic position tracking system, in accordance with an embodiment of the present invention.

FIG. 1 is a schematic pictorial illustration of a fluoroscopic imaging system 22 and a magnetic position tracking system 20 applied in a medical procedure, in accordance with an embodiment of the present invention.

A cardiologist 42 (or any other qualified user) navigates catheter 24 in a heart 28 of a patient 30 (shown in an inset 32) using a position sensor 41 installed near the distal end of the catheter, until distal end 34 reaches the desired location. Cardiologist then performs a desired medical procedure, such as ablation or mapping, using catheter 24. Position sensor 41 is configured to sense magnetic fields generated by field-generators 36A-36D and to transmit signals to a processor 44 for determining of the distal end, e.g., six dimensional position and orientation coordinates (X,Y,Z, pitch, yaw, roll).

Magnetic position tracking is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

A console 26 comprises processor 44, a driver circuit 50, an interface 48 to fluoroscopic imaging system 22, input devices 46, and a display 40. System 20 comprises a low-profile location pad 38 that may be rectangular, although other suitable shapes can also be used. The dimensions of pad 38 are typically about 1.2 cm in thickness and 50 cm in length and width, although other shapes and corresponding dimensions may be used. The pad comprises a frame 37 and one or more magnetic field-generators, such as field-generating coils, fixed on frame 37. In the exemplary configuration shown in an inset 29 of FIG. 1, pad 38 comprises four field-generators 36A-36D.

The location pad is placed on top of a catheterization table 33 and under the patient's torso, such that generators 36A-36D are located at fixed, known positions external to the patient. In alternative embodiments, pad 38 may comprise three generators, or any other suitable number. Driver circuit 50 drives field-generators 36A-36D with suitable signals so as to generate magnetic fields in a predefined working volume around heart 28.

In an embodiment, a mattress 35 is placed beneath patient 30 and pad 38 is located beneath the mattress and above table 33. In another embodiment, the field-generators are attached to the patient's torso and the patient lying directly on table 33. In an alternative embodiment, pad 38 is located beneath table 33. In case a fluoroscopic image is needed, cardiologist 42 uses input devices 46 and a suitable Graphical User Interface (GUI) on display 40 to request a fluoroscopic image in patient's heart 28. Processor 44 is configured to calculate and display a Region-of-Interest (ROI) 39 to be irradiated by system 22.

Referring to an inset 27, generators 36A-36D are typically located around ROI 39. In an embodiment, pad 38 comprises an open-frame 37 around ROI 39 so as to allow irradiated X-rays from system 22 to pass through the open side of pad 38. As can be seen in the figure, the open side of frame 38 faces the fluoroscopic system. In this arrangement, location pad 38 causes little or no obstruction or shadowing to the fluoroscopic imaging, at least in most commonly-used fluoroscopic projections (e.g., AP, LAO and RAO).

A traditional close-frame pad may block some of the X-rays and thus, blocking required cardiac imaging from cardiologist 42 and reducing the effective size of ROI 39. The disclosed technique overcomes this limitation by eliminating one side or any other suitable part of frame 37 so as to provide the user with imaging of the full area of ROI 39. Additional embodiments of the pad are described in greater details in FIGS. 2A and 2B.

Although FIG. 1 shows a system for cardiac catheterization, open-frame location pads such as pad 38 can be used in any other position tracking application, such as for tracking orthopedic implants and various medical tools. In the example of FIG. 1 the location pad is placed horizontally and has a reduced height or vertical dimension. The methods and devices described herein can be used to reduce any desired dimension of the location pad, as appropriate for the particular application. Additionally, the methods and systems described herein can also be used in other applications that involve simultaneous mapping and Fluoroscopic imaging.

Figure 2A:
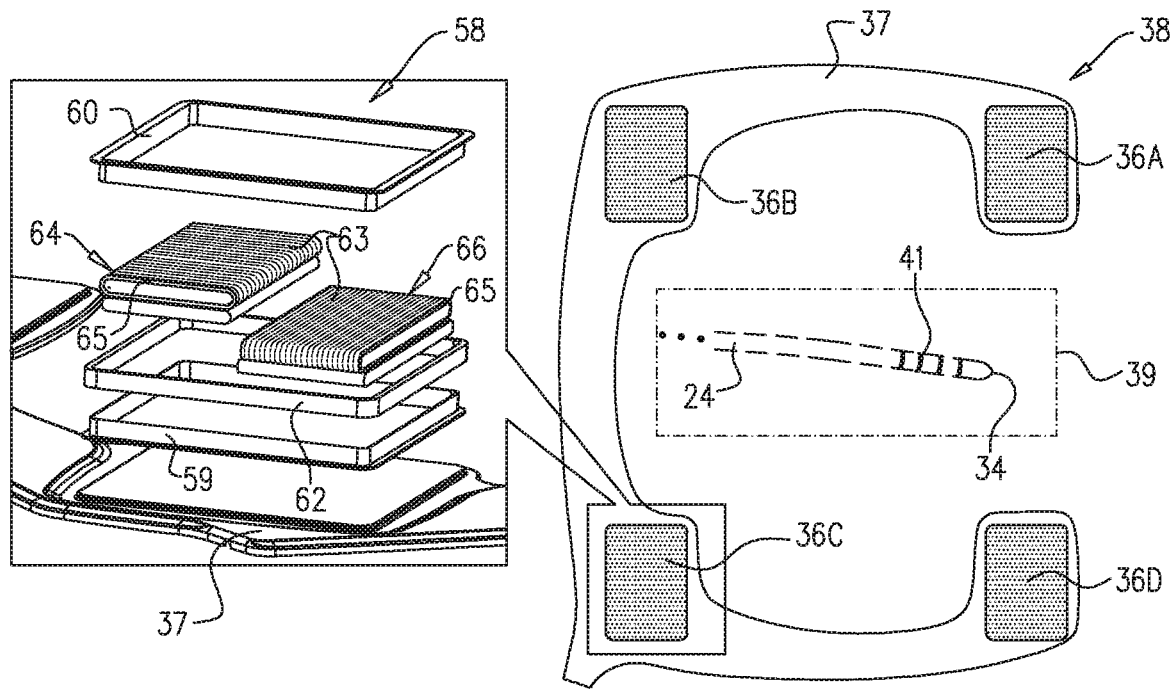
FIG. 2A is a schematic top-view of an open-frame low-profile location pad, in accordance with an embodiment of the present invention.

FIG. 2A is a schematic top-view of open-frame low-profile location pad 38, in accordance with an embodiment of the present invention. Pad 38 comprises open-frame 37 on which generators 36A-36D are arranged in a planar rectangular configuration. The distance between any pair of field-generators is typically in the range of several centimeters to several tens of centimeters (e.g., 8-55 cm), although other distances can also be used.

The figure also illustrates ROI 39 of fluoroscopic system 22. Distal end 34 of catheter 24 is located within ROI 39. Position sensor 41, which is installed near the distal end of the catheter, is configured to sense the magnetic fields from field-generators 36A-36D so as to form six dimensional position and orientation coordinates of the distal end. Field-generators 36A-36D of pad 38 are typically arranged around ROI 39 in any suitable arrangement, such as on a triangle or a rectangle. In the example of FIG. 2A, pad 38 comprises four field-generators 36A-36D that are arranged in a rectangular shape and fixed on frame 37.

An inset 58 comprises an exploded view of field-generator 36C, which is substantially similar to field-generators 36A, 36B, and 36D, and is fixed on frame 37. In some embodiments, field-generator 36C comprises a base-frame 59, three non-concentric orthogonal coils 62, 64 and 66, arranged adjacent to one another within the base-frame, and a cap 60, which encloses the coils within the base-frame. In other embodiments, at least two of the coils, but not necessarily all the coils, are non-concentric.

In yet other embodiments, the coils may be arranged relative to one another in any non-parallel configuration that may not be necessarily orthogonal. Thus, the respective generated magnetic fields are not parallel, however not necessarily orthogonal to one another.

As can be seen in the figure, coils 62, 64 and 66 are wound and oriented in three mutually-orthogonal axes. Each coil is thus configured to generate a magnetic field component in one direction out of three mutually-orthogonal directions. Coils 64 and 66 typically comprise flat coils typically in the range of 6-10 mm (e.g., 8 mm) thick and are located side-by-side in a single plane whereas coil 62 is located around them. This arrangement allows packaging the three non-concentric coils in a planar field-generator.

In an embodiment, each coil (e.g., coils 62, 64, 66) comprises a fiber core 65, typically made of carbon, and wires 63, typically made of copper. Wires 63 are wrapped around core 65. The coils are typically in the range of 6-10 mm (e.g., 8 mm) thick and the overall dimension of pad 38 may be 50 cm or any other suitable size. Each coil generates a magnetic field typically in a direction orthogonal to the orientation of the coil wrappings, when applying electrical current to the wires of the coil.

In alternative embodiments, each field-generator may comprise three concentric coils. Such configuration, however, typically results in a thicker field-generator.

In some embodiments, frame 37 comprises three solid arms that are made of a suitable material such as plastic or fiberglass. The fourth side of the rectangle (e.g., the side between field-generators 36A and 36D) is deliberately open so as to form the open-frame. As shown in FIG. 1, the open side is located below patient's heart 28 and thus enables unobstructed fluoroscopic imaging throughout ROI 39.

In the context of the present patent application and in the claims, the terms "open" and "open side" refer to a side of frame 37 that is transparent to X-ray radiation, and therefore invisible to fluoroscopic system 22. In alternative embodiments, the open side may be mechanically closed to some extent, as long as transparency to X-ray radiation is maintained. Such configurations may enable unobstructed fluoroscopic imaging, and at the same time provide sufficient mechanical rigidity to the location pad. For example, field-generators 36A and 36D may be connected by an arm made of a material transparent to X-ray radiation, by a perforated arm that allows a sufficient portion of the X-ray radiation to pass through, or by any other means.

Figure 2B:
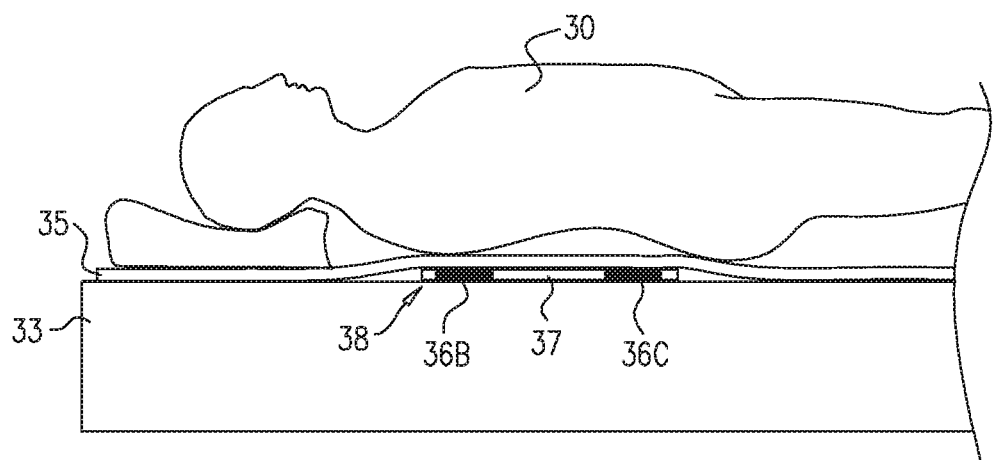
FIG. 2B is a schematic side-view of an open-frame low-profile location pad, in accordance with an embodiment of the present invention.

FIG. 2B is a schematic side-view of pad 38, in accordance with an embodiment of the present invention. Pad 38 comprises low-profile frame 37 formed by frame material with a typical thickness of 1.2 cm. Generators 36B and 36C are fixed on frame 37 (together with generators 36A and 36D, which are invisible in this side-view). In some embodiments, pad 38 is located between table 33 and mattress 35 on which patient 30 lies.

The low profile of pad 38 allows positioning the pad directly on table 33 and beneath the patient without causing inconvenience. Using mattress 35 may be optional, and in alternative embodiments, pad 38 may be formed to provide the required flatness and convenience for patient 30, so as to allow direct contact between the patient's torso and respective generators 36A-36D.

The close proximity of pad 38 to patient 30 (and therefore to the position sensor on the distal end of catheter 24), reduces shadowing effects that the pad may have on the X-rays. This effect is especially noticeable while irradiating patient 30 by system 22 at an angle that is not orthogonal to the plane of the location pad. Additionally, the close proximity between the location pad and the catheter may improve the measurement accuracy of the location of the distal end.

Figure 3:
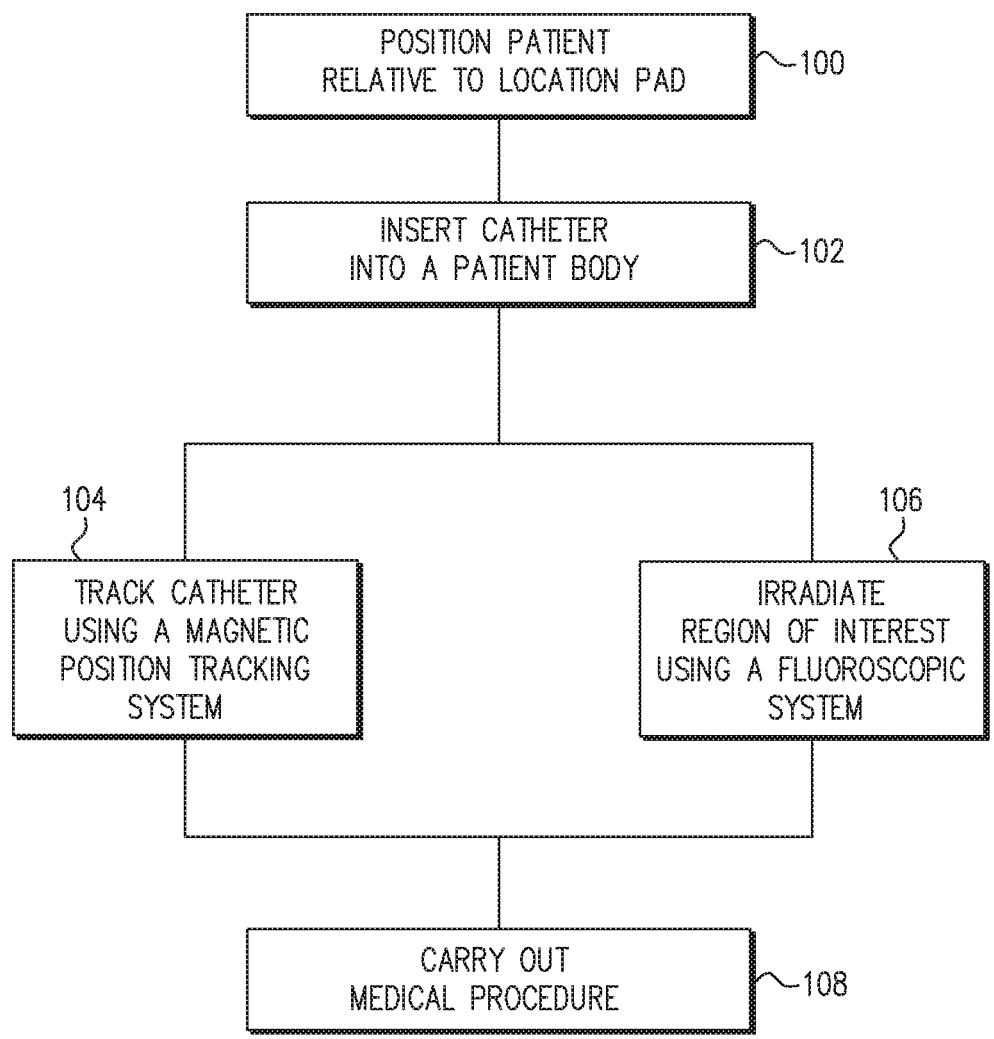
FIG. 3 is a flow chart that schematically illustrates a method for simultaneous imaging and position tracking, in accordance with embodiments of the present invention.

FIG. 3 is a flow chart that schematically illustrates a method for simultaneous imaging and position tracking during a catheterization procedure, in accordance with embodiments of the present invention. The method begins by positioning patient 30 on table 33, relative to location pad 38, wherein the pad is positioned between the table and the patient's torso, at a patient positioning step 100. The cardiologist inserts catheter 24 into the patient body, at a catheter insertion step 102. During the catheterization procedure, the cardiologist tracks the position of distal end 34 in the patient's heart using magnetic position system 20, at a tracking step 104. In parallel, the cardiologist may decide to irradiate ROI 39 of the patient using system 22, at an irradiation step 106. The disclosed techniques allow unobstructed imaging of ROI 39 that provides the cardiologist with the required fluoroscopic images so as to carry out ablation of the respective tissue, at a procedure carry out step 108.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A field generator, comprising:
three non-concentric orthogonal coils
wherein the three non-concentric orthogonal coils comprise a first coil, a second coil, and a third coil, wherein in the field generator the first coil and the second coil are located side-by-side and the third coil is located around the first coil and the second coil,
the first coil comprising first wires wrapped around a first core,
the second coil comprising second wires wrapped around a second core,
the third coil comprising third wires wrapped around the first coil, the second coil, and a third core,
wherein the first coil and the second coil are disposed on the third core.

2. The field generator according to claim 1, wherein the three non-concentric orthogonal coils are arranged in a single plane.

3. The field generator according to claim 1, wherein each of the coils has a height between 6 mm and 10 mm.

4. A method for producing a field generator, the method comprising:
providing three coils; and
arranging the coils such that the coils are non-concentric and the coils are wound and oriented in three mutually-orthogonal axes, each of the coils being configured so as to generate a magnetic field component in one direction out of three mutually-orthogonal directions,
wherein the three non-concentric orthogonal coils comprise a first coil, a second coil, and a third coil, wherein in the field generator the first coil and the second coil are located side-by-side and the third coil is located around the first coil and the second coil, the first coil comprising first wires wrapped around a first core, the second coil comprising second wires wrapped around a second core, the third coil comprising third wires wrapped around the first coil, the second coil, and a third core, wherein the first coil and the second coil are disposed on the third core.

5. The method according to claim 4, wherein arranging the coils comprises arranging the three non-concentric orthogonal coils in a single plane.

6. The method according to claim 4, wherein each of the coils has a height between 6 mm and 10 mm.

7. A method for generating magnetic fields, the method comprising:

providing a field generator, comprising three non-concentric orthogonal coils; and driving electrical currents into the coils so as to generate respective magnetic field components having mutually-orthogonal directions, wherein the three non-concentric orthogonal coils comprise a first coil, a second coil, and a third coil, wherein in the field generator the first coil and the second coil are located side-by-side and the third coil is located around the first coil and the second coil, the first coil comprising first wires wrapped around a first core, the second coil comprising second wires wrapped around a second core, the third coil comprising third wires wrapped around the first coil, the second coil, and a third core, wherein the first coil and the second coil are disposed on the third core.

* * * * *